(12) United States Patent
Tsinberg

(10) Patent No.: US 12,741,040 B2
(45) Date of Patent: Sep. 22, 2026

(54) ULTRASOUND-BASED VIRUS SHIELD

(71) Applicant: KEY DIGITAL SYSTEMS, INC., Mount Vernon, NY (US)

(72) Inventor: Mikhail Tsinberg, New York, NY (US)

(73) Assignee: KEY DIGITAL SYSTEMS, INC., Mount Vernon, NY (US)

( * ) Notice: Subject to any disclaimer, the term of this patent is extended or adjusted under 35 U.S.C. 154(b) by 1186 days.

(21) Appl. No.: 17/715,199

(22) Filed: Apr. 7, 2022

(65) Prior Publication Data

US 2022/0331461 A1 Oct. 20, 2022

Related U.S. Application Data

(60) Provisional application No. 63/174,748, filed on Apr. 14, 2021.

(51) Int. Cl.

*A61L 2/025* (2006.01)
*A61L 2/26* (2006.01)
*G01S 15/08* (2006.01)

(52) U.S. Cl.

CPC ................. *A61L 2/025* (2013.01); *A61L 2/26* (2013.01); *G01S 15/08* (2013.01)

(58) Field of Classification Search

CPC ... A61L 2/025; A61L 2/26; A61L 9/16; G01S 15/08; G01S 15/04; G01S 15/102; G01S 15/87; G01S 15/88; G01S 7/521

See application file for complete search history.

(56) References Cited

U.S. PATENT DOCUMENTS 8,600,374 B1 * 12/2013 Hertlein .................. H04M 1/18 455/425

2010/0321180 A1 * 12/2010 Dempsey ........... G08B 13/1427 340/539.12

* cited by examiner

*Primary Examiner* — Brendan A Hensel

(74) *Attorney, Agent, or Firm* — ArentFox Schiff LLP

(57) ABSTRACT

Described herein is an ultrasound-based virus shield. The ultrasound-based virus shield may include an ultrasound sonar emitter configured to emit a first sonar signal including a header with key data, and an ultrasound sonar receiver configured to receive a second sonar signal. The ultrasound-based virus shield may include a processor configured to: calculate a distance between the ultrasound-based virus shield and a subject in response to determining that the second sonar signal includes the key data associated with the first sonar signal, and activate an ultrasound sterilizing emitter in response to determining that the distance calculated is less than a threshold distance. An ultrasound sterilizing emitter of the ultrasound-based virus shield may be configured to emit a sterilizing signal.

19 Claims, 12 Drawing Sheets

500

600

700

800

850

Tie Add-on

Eyewear Add-on

Pocket Add-on

ULTRASOUND-BASED VIRUS SHIELD

CROSS-REFERENCE TO RELATED APPLICATIONS

This application claims the benefit of U.S. Provisional Application No. 63/174,748, filed Apr. 14, 2021, which is herein incorporated by reference.

FIELD OF TECHNOLOGY

The present disclosure relates to the field of biotechnology, and, more specifically, to an ultrasound-based virus shield.

BACKGROUND

Viruses may be both extremely dangerous and difficult to control in a large group setting. Depending on how contagious the virus is, the spread may lead to an epidemic or in the worst case scenario—a pandemic. A clear example of this is the coronavirus (COVID-19). To combat the spread of the coronavirus, masks began to be widely used. However, a majority of the masks were either surgical masks or fabric masks usually made of cotton. These masks are somewhat adequate for blocking particles coming from mouths and noses, but they do not eliminate viruses or sterilize surfaces. At best, particles stay on the surface of the mask and are not ingested by the wearer. These particles can easily be ingested if, for example, the person removes the mask with his/her hands and proceeds to make contact with another part of their body without washing the hands (e.g., rubbing his/her eyes).

Furthermore, because some people experience difficulties wearing face coverings over a long period of time, these masks lack a comfort factor. As a result, some people actively choose to remove the mask and risk potential exposure to any viruses.

There thus exists a need for a solution that can eliminate viruses (not just attempt to block them) and not seem like a nuisance, in terms of comfort, to a user.

SUMMARY

Aspects of the disclosure relate to an ultrasound-based virus shield that addresses the needs outlined previously.

In one exemplary aspect, the ultrasound-based virus shield may include an ultrasound sonar emitter configured to emit a first sonar signal including a header with key data, and an ultrasound sonar receiver configured to receive a second sonar signal. The ultrasound-based virus shield may include a processor configured to: calculate a distance between the ultrasound-based virus shield and a subject in response to determining that the second sonar signal includes the key data associated with the first sonar signal, and activate an ultrasound sterilizing emitter in response to determining that the distance calculated is less than a threshold distance. An ultrasound sterilizing emitter of the ultrasound-based virus shield may be configured to emit a sterilizing signal.

In some aspects, the techniques described herein relate to an ultrasound-based virus shield, wherein the processor is further configured to ignore the second sonar signal in response to determining that the second sonar signal does not include the key data associated with the first sonar signal.

In some aspects, the techniques described herein relate to an ultrasound-based virus shield, the processor is further configured to calculate the distance by executing a function that converts a time difference between the first sonar signal and the second sonar signal to the distance.

In some aspects, the techniques described herein relate to an ultrasound-based virus shield, wherein the ultrasound sonar emitter is configured to emit the sterilizing signal until the distance between the ultrasound-based virus shield and the subject is not greater than the threshold distance.

In some aspects, the techniques described herein relate to an ultrasound-based virus shield, wherein the ultrasound sonar emitter is configured to emit the sterilizing signal for an additional time period associated with post detection hysteresis after the distance between the ultrasound-based virus shield and the subject is greater than the threshold distance.

In some aspects, the techniques described herein relate to an ultrasound-based virus shield, wherein the ultrasound sonar emitter and the ultrasound sterilizing emitter emit the first sonar signal and the sterilizing signal, respectively, at different ultrasound frequencies to limit interference.

In some aspects, the techniques described herein relate to an ultrasound-based virus shield, wherein the ultrasound sonar emitter and the ultrasound sterilizing emitter emit the first sonar signal and the sterilizing signal, respectively, at different time slots to limit interference.

In some aspects, the techniques described herein relate to an ultrasound-based virus shield, wherein the sterilizing signal includes a broadcast of at least one square wave carrier in a frequency band.

In some aspects, the techniques described herein relate to an ultrasound-based virus shield, wherein a duty cycle, a frequency position, and an amplitude of the at least one square wave carrier is adjustable based on virus characteristics that the ultrasound-based virus shield is configured to eliminate.

In some aspects, the techniques described herein relate to an ultrasound-based virus shield, wherein a frequency position of the at least one square wave carrier is changed a number of times within a threshold period of time.

In some aspects, the techniques described herein relate to an ultrasound-based virus shield, further including: a communication component configured to transmit signal and distance information to a virus shield application installed on a computing device.

In some aspects, the techniques described herein relate to an ultrasound-based virus shield, further including a communication component configured to connect with a second ultrasound-based virus shield within a connective range. In some aspects, the processor is further configured to instruct the second ultrasound-based virus shield to not activate a second ultrasound sterilizing emitter of the second ultrasound-based virus shield in response to determining that the ultrasound sterilizing emitter of the ultrasound-based virus shield is emitting the sterilizing signal.

In some aspects, the techniques described herein relate to an ultrasound-based virus shield, wherein the processor is further configured to instruct the second ultrasound-based virus shield to not activate the second ultrasound sterilizing emitter in further response to determining that a remaining battery life of the second ultrasound-based virus shield is less than a remaining battery life of the ultrasound-based virus shield.

In some aspects, the techniques described herein relate to an ultrasound-based virus shield, wherein the processor is further configured to instruct the second ultrasound-based virus shield to not activate the second ultrasound sterilizing emitter in further response to determining that an anticipated usage of the second ultrasound sterilizing emitter is greater than an anticipated usage of the ultrasound sterilizing emitter.

In some aspects, the techniques described herein relate to an ultrasound-based virus shield, further including a strap that fixes the ultrasound-based virus shield around a head or neck of a wearer.

In some aspects, the techniques described herein relate to an ultrasound-based virus shield, wherein the ultrasound sonar emitter includes multiple emitters that each emit a portion of the first sonar signal, and wherein the first sonar signal achieves 360 degree coverage around the wearer.

In some aspects, the techniques described herein relate to an ultrasound-based virus shield, wherein the ultrasound sterilizing emitter directs the sterilizing signal towards a face of the wearer.

In some aspects, the techniques described herein relate to an ultrasound-based virus shield, wherein the ultrasound sterilizing emitter includes multiple emitters that each emit a portion of the sterilizing signal.

In some aspects, the techniques described herein relate to an ultrasound-based virus shield, further including an attaching component that fixes the ultrasound-based virus shield to a surface.

In some aspects, the techniques described herein relate to an ultrasound-based virus shield, wherein the attaching component is one of a clip, an adhesive, a pin, and a mounting bracket.

In some aspects, the techniques described herein relate to a method for sterilizing a virus using an ultrasound-based virus shield, the method including: emitting a first sonar signal including a header with key data; receiving a second sonar signal; determining whether the second sonar signal includes the key data associated with the first sonar signal; calculating a distance between the ultrasound-based virus shield and a subject in response to determining that the second sonar signal includes the key data associated with the first sonar signal; determining whether the distance calculated is less than a threshold distance; and emitting a sterilizing signal in response to determining that the distance calculated is less than the threshold distance.

It should be noted that the methods described above may be implemented in a system comprising a hardware processor. Alternatively, the methods may be implemented using computer executable instructions of a non-transitory computer readable medium.

The above simplified summary of example aspects serves to provide a basic understanding of the present disclosure. This summary is not an extensive overview of all contemplated aspects, and is intended to neither identify key or critical elements of all aspects nor delineate the scope of any or all aspects of the present disclosure. Its sole purpose is to present one or more aspects in a simplified form as a prelude to the more detailed description of the disclosure that follows. To the accomplishment of the foregoing, the one or more aspects of the present disclosure include the features described and exemplarily pointed out in the claims.

BRIEF DESCRIPTION OF THE DRAWINGS

The accompanying drawings, which are incorporated into and constitute a part of this specification, illustrate one or more example aspects of the present disclosure and, together with the detailed description, serve to explain their principles and implementations.

DETAILED DESCRIPTION

Exemplary aspects are described herein in the context of a system, method, and computer program product for sterilizing a virus using an ultrasound-based virus shield. Those of ordinary skill in the art will realize that the following description is illustrative only and is not intended to be in any way limiting. Other aspects will readily suggest themselves to those skilled in the art having the benefit of this disclosure. Reference will now be made in detail to implementations of the example aspects as illustrated in the accompanying drawings. The same reference indicators will be used to the extent possible throughout the drawings and the following description to refer to the same or like items.

To overcome the shortcomings of traditional masks, the present disclosure describes a virus shield that sterilizes viruses using ultrasound beams. The virus shield may come in multiple variations including, but not limited to, a headband, a necklace, glasses, a clip, or any other near-head wearable. In each variation, the virus shield is equipped with ultrasound sterilizing emitters that sterilize viruses such as the coronavirus before they reach the face of a wearer. While ultrasound is used for sterilization, any solution that uses wireless signals (e.g., radiofrequency, light, X-rays, etc.) may be incorporated in the emitters of the virus shield of the present disclosure. In an exemplary aspect, the virus shield is further equipped with ultrasound sonar emitters configured to detect the presence of other humans in close proximity to the wearer and activate the sterilizing function in an energy efficient manner.

Figure 1:
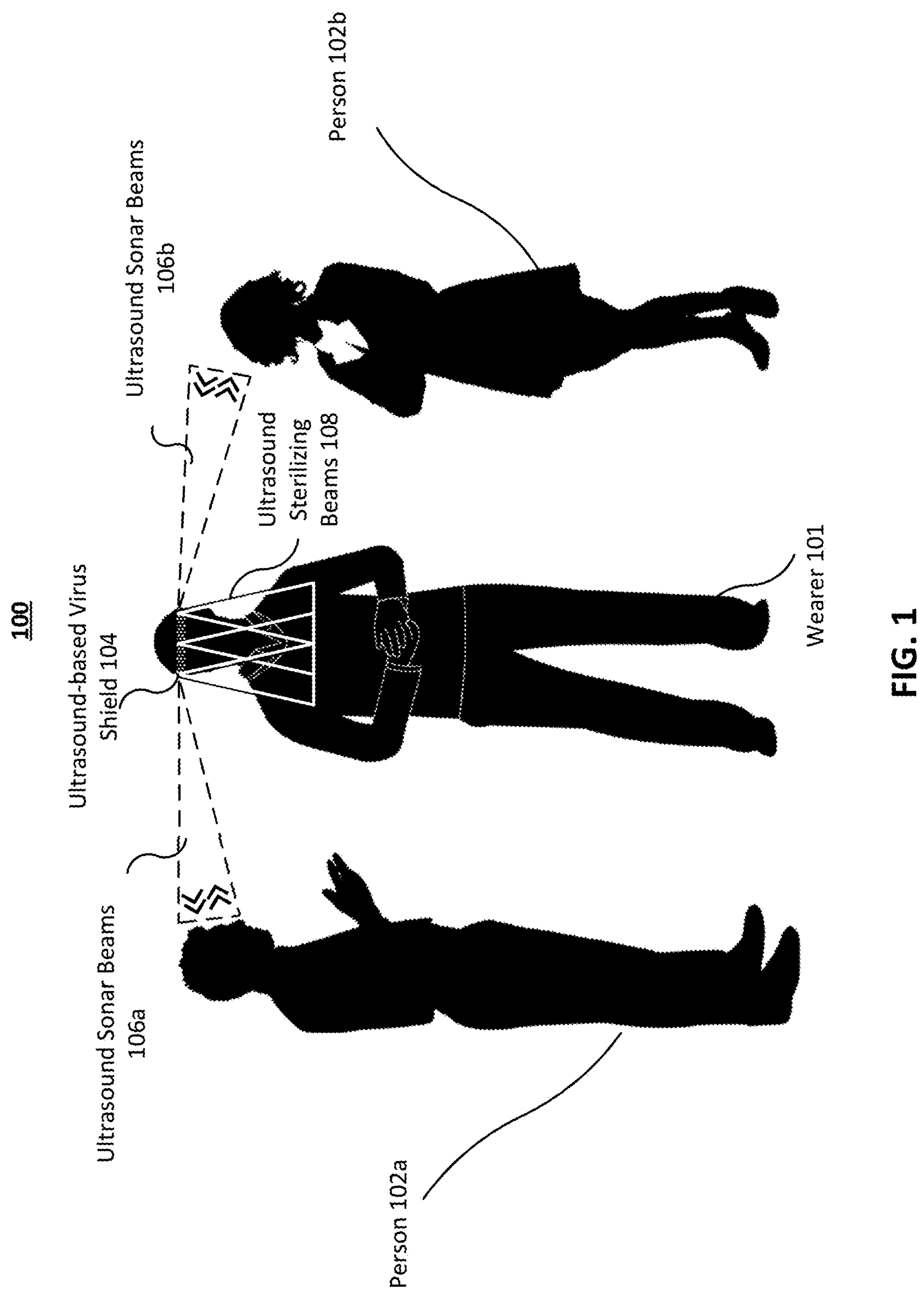
FIG. 1 is a diagram illustrating usage of a variation of the ultrasound-based virus shield.

FIG. 1 is diagram 100 illustrating usage of a variation of the ultrasound-based virus shield. This variation of the virus shield is a headband/head covering. In diagram 100, wearer 101 is wearing ultrasound-based virus shield 104 around the forehead. Person 102*a* and person 102*b* may be in close proximity to wearer 101 (i.e., within a threshold distance such as 2 meters). Ultrasound-based virus shield 104 emits ultrasound sonar beams 106*a* and 106*b*, and receives reflections that indicate the presence of person 102*a* and 102*b*, respectively, in close proximity to wearer 101. In response to detecting person 102*a* and/or person 102*b*, ultrasound-based virus shield 104 emits ultrasound sterilizing beams 108 towards the face of wearer 101. Sterilizing beams 108 eliminate viruses, which may be airborne or on the surface of wearer 101, near the face of wearer 101. Unlike a traditional mask that blocks the nose and mouth—causing breathing difficulties—ultrasound-based virus shield 104 does not block the face of wearer 101.

Figure 2:
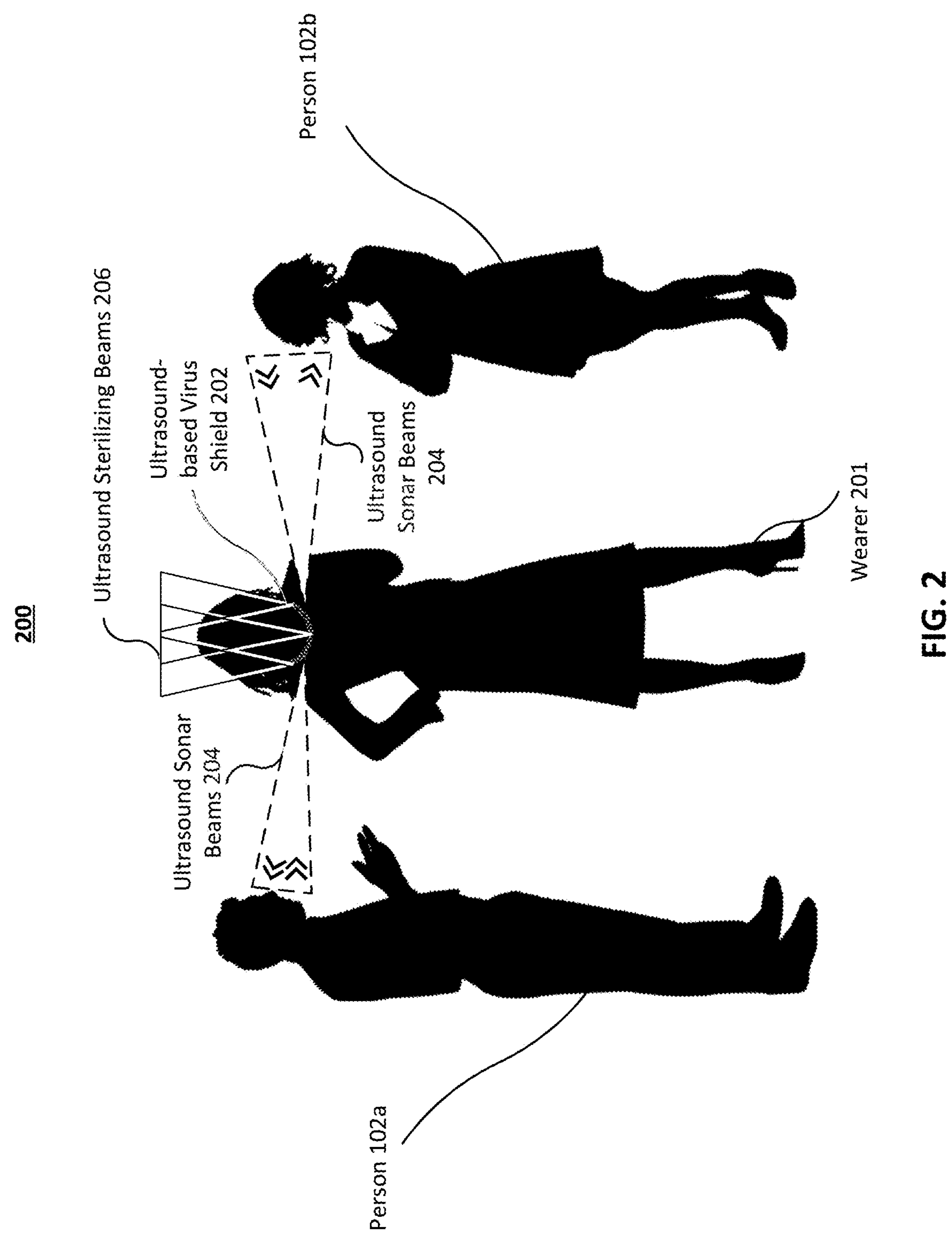
FIG. 2 is a diagram illustrating usage of another variation of the ultrasound-based virus shield.

FIG. 2 is diagram 200 illustrating usage of another variation of the ultrasound-based virus shield. This variation of the virus shield is a necklace. As such, in diagram 200, wearer 201 is wearing ultrasound-based virus shield 202 around the neck. Similar to the first variation described, ultrasound-based virus shield 202 emits ultrasound sonar beams 204 to detect person 102*a* and person 102*b*. In response to detecting person 102*a* and/or person 102*b*, ultrasound-based virus shield 202 emits ultrasound sterilizing beams 206 towards the face of wearer 201. It should be noted that virus shield 104 directs sterilizing beams downward and virus shield 202 directs sterilizing beams upward. Because the nose, eyes, and mouth are entry points and exit points for viruses, ultrasound-based virus shield 104 and ultrasound-based virus shield 202 have sterilizing beam emitters directed towards these entry points and exit points. Nonetheless, a user may also sterilize their hands and other objects if they place them in the range of the ultrasound sterilizing beams.

Figure 3:
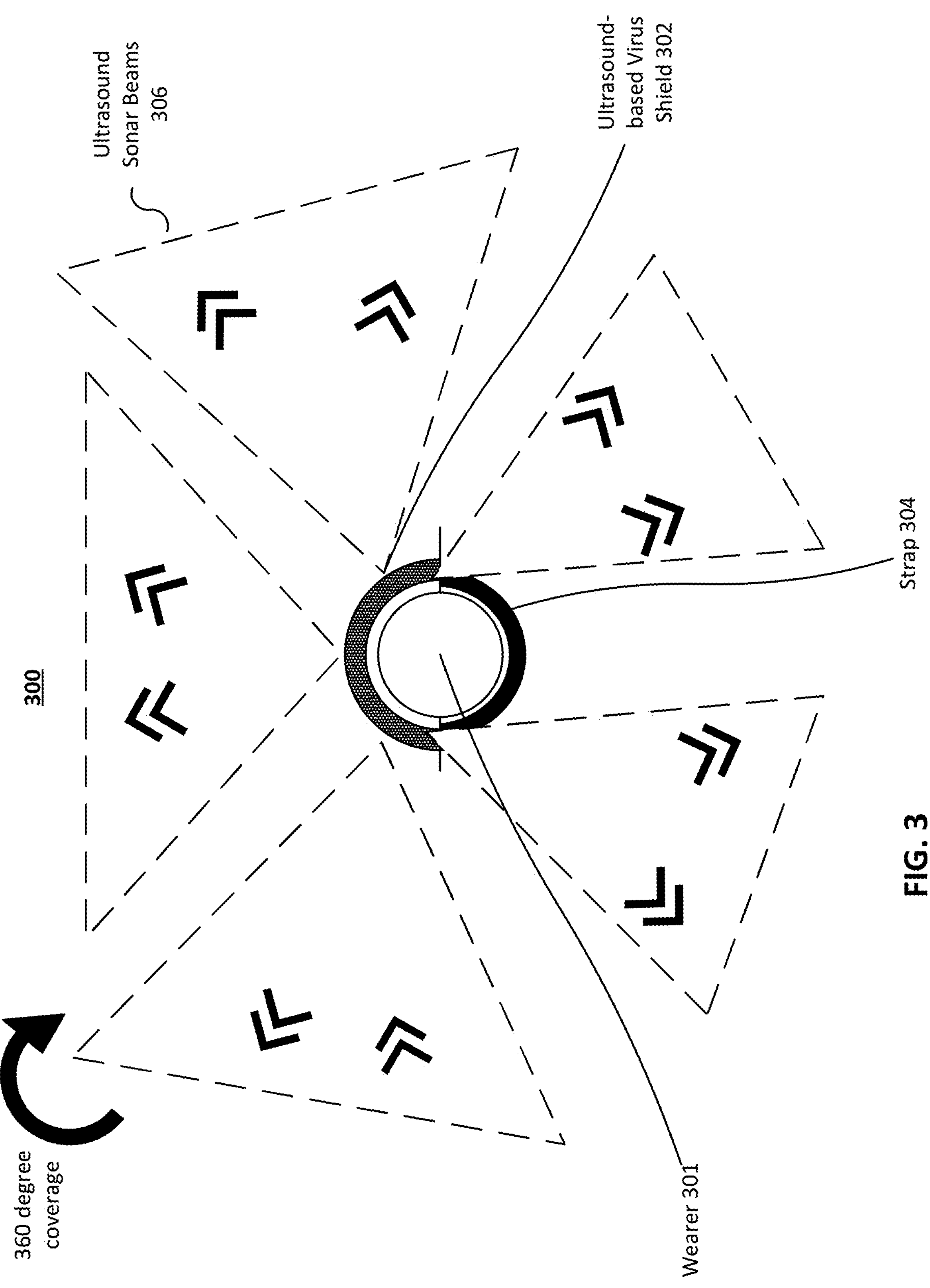
FIG. 3 is a diagram illustrating a top view of the ultrasound-based virus shield emitting ultrasound beams.

FIG. 3 is diagram 300 illustrating a top view of the ultrasound-based virus shield emitting ultrasound beams. The center circle in diagram 300 represents a head of wearer 301. Ultrasound-based virus shield 302 may be a headband or a necklace. In some aspects, ultrasound-based virus shield 302 may be connected to strap 304, which fixes the shield around the head or the neck of a wearer. For example, strap 304 may be a chain, a band, a buckle, a magnet, or any other connective object.

As shown in diagram 300, ultrasound sonar beams 306 have 360 degree coverage around wearer 301. Therefore, even if person 102*a* is behind wearer 301, detection is possible and sterilization can be activated. It should be noted that although ultrasound sonar beams 306 are not originating from strap 304, the length of ultrasound-based virus shield 302 may be longer or shorter to enable 360 degree coverage. In some aspects, the length of ultrasound-based virus shield 302 is adjustable by the wearer. In some aspects, strap 304 may be a portion of ultrasound-based virus shield 302, and may include sonar beam emitter(s).

Figure 4:
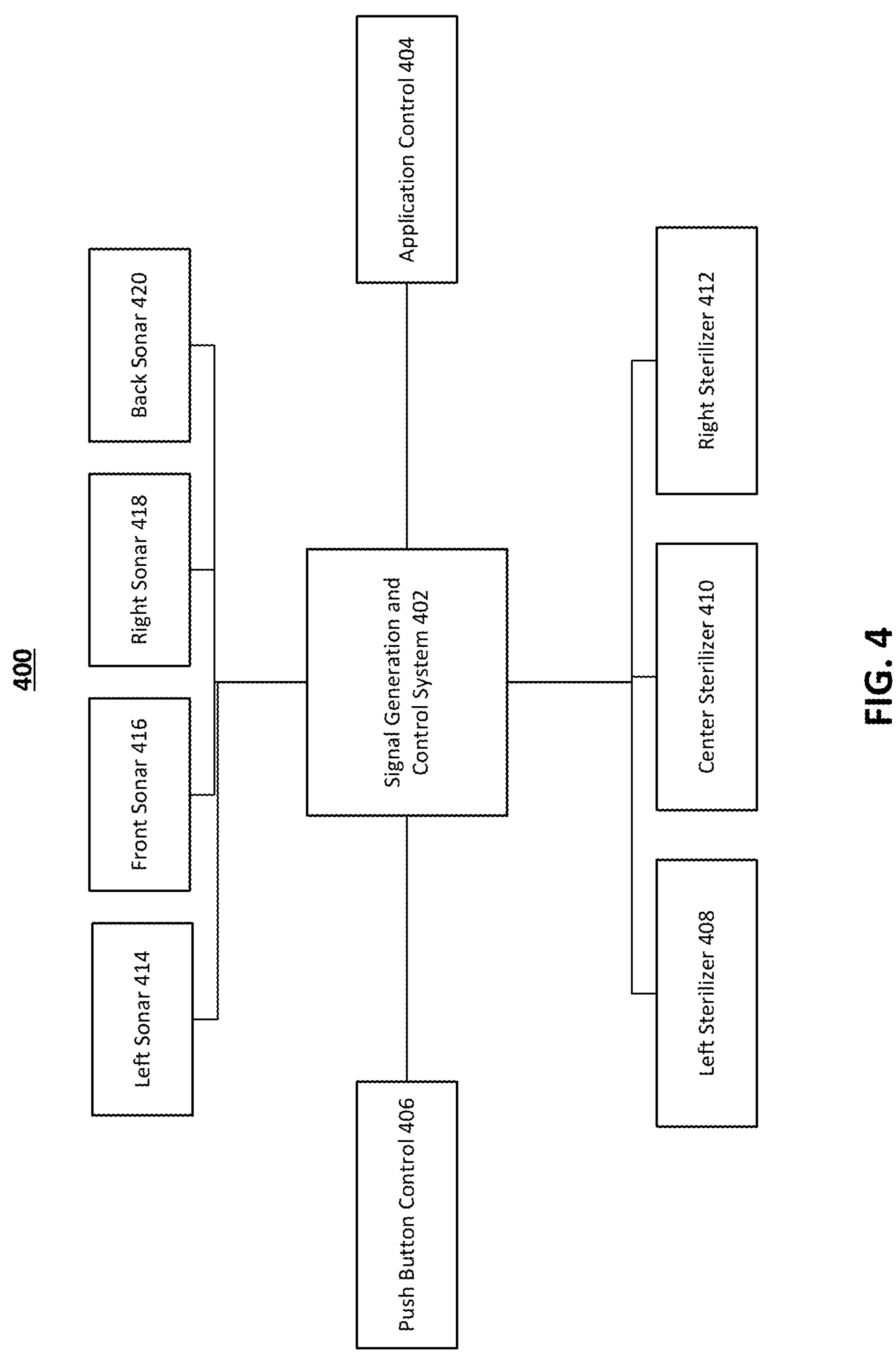
FIG. 4 is a block diagram illustrating components of a ultrasound-based virus shield.

FIG. 4 is block diagram 400 illustrating components of a ultrasound-based virus shield. Each of the components, for example, may be built into ultrasound-based virus shield 302. Accordingly, the combination of left sonar 414, front sonar 416, right sonar 418, and back sonar 420 may produce ultrasound sonar beams 306 (depicted simplistically as five dashed triangles). Signal generation and control system 402 is configured to activate and deactivate a plurality of sonar and sterilizing emitters. For example, in diagram 400, signal generation and control system 402 is connected to left sonar emitter/receiver 414, front sonar emitter/receiver 416, right sonar emitter/receiver 418, and back sonar emitter/receiver 420. The combination of these emitters directed towards the direction implied by their names enables the 360 degree coverage described in diagram 300. It should be noted that although four emitters are depicted, one skilled in the art will appreciate that any number of sonar emitters may be attached to the ultrasound-based virus shield. For example, there may be two back sonar emitters.

Signal generation and control system 402 is further connected to left sterilizer 408, center sterilizer 410, and right sterilizer 412. Similar to the sonar emitters, any number of sterilizers may be included on the virus shield such that virus access to the entry points of the human face is prevented. For example, if center sterilizer 410 has a long range, left sterilizer 408 and right sterilizer 412 may not be needed. Depending on the variation of the virus shield, the left and right sterilizers may thus be omitted from the design. In contrast, depending on the variation of the virus shield, there may also be multiple center sterilizers as an added defense against viruses. There are two primary differences between sterilizers and emitters. Firstly, a sonar emitter has lower power and a narrow band speaker to send a single modulated frequency. A microphone of the sonar emitter catches the reflections of the outputted sonar waves. Secondly, a sterilizer has a wide band speaker and outputs with greater power in short periods of time. The powerful speaker is needed to kill viruses in the vicinity of the sterilizer.

In some aspects, co-location sonar and sterilizing emitters may be on the same unit with controlled emission power (e.g., weaker for sonar and stronger for sterilizing). For example, left sonar 414 and left sterilizer 408 may be a single unit. In other aspects, sonar and sterilizing emitters may use different frequencies and/or different time slots to avoid interference with each other or other virus shield devices. For example, right sonar 418 may emit a sonar beam at a different time than right sterilizer 412, and/or may emit at a different frequency than right sterilizer 412.

In some aspects, signal generation and control system 402 may be connected to push button control 406 and application control 404. For example, there may be a physical button or touchpad on the ultrasound-based virus shield that is configured to receive inputs from the wearer. By accessing push button control 406, a user may be able to, for example, manually activate and/or deactivate different emitters on the virus shield. A user may also be able to start a connection with a computing device (e.g., a smartphone) via Wi-Fi or Bluetooth through a series of presses and/or long presses.

Application control 404, which is a communication component of the virus shield, exchanges information with an application installed on a computing device (e.g., a virus shield application). The application may present a user with functionality/settings of the virus shield and may enable user configurations. For example, a user may be able to activate/deactivate specific emitters (e.g., to increase performance or battery life). Application control 404 may also allow a user to adjust the amount of time during which sterilizing and/or sonar beams are emitted, sleep times (e.g., to prevent prolonged use), proximity distances for each sonar emitter (e.g., to adjust how close another person needs to be before activating sterilization), etc. If a user makes a change in functionality, the virus shield application transmits the change to application control 404, which subsequently adjusts signal generation and control system 402.

Application control 404 may also provide the virus shield application with historic information such as when sterilization was activated, the amount of time spent sterilizing, when sonar beams were emitted, the amount of time spent detecting other persons, battery drainage over time, etc. The virus shield application may present this data to the user as a report in a graphical user interface (GUI). In some aspects, a user may manually enable sterilization using push button control 406 or application control 404 (e.g., via the virus shield application).

In some aspects, application control 404 may communicate with another application control 404 of a different ultrasound-based virus shield. In some aspects, data exchange by means of ultrasound communication can be used as a personal hotspot allowing one computing device to use the Internet (or any other network access) of a different computing device.

Suppose that in diagram 100, person 102*a* and person 102*b* also wore ultrasound-based virus shields. Application control 404 of each shield may communicate with each other to enable an energy-efficient sterilization process. For example, if person 102*a* and wearer 101 are within a threshold distance such that the ultrasound sterilizing beams of virus shield 104 can adequately eliminate the viruses near person 102*a*, then the virus shield worn by person 102*a* is instructed, via application control 404 of virus shield 104, to not emit sterilizing beams, emit sterilizing beams for a shorter period of time, or emit sterilizing beams at a lower intensity/power. In some aspects, the instructions may also incorporate directions. For example, if person 102*a* is on the right side of wearer 101, application control 404 of virus shield 104, may instruct the virus shield worn by person 102*a* to only activate center sterilizer 410 and right sterilizer 412 because the sterilization beams from virus shield 104 adequately cover the area that left sterilizer 408 would cover.

In general, signal generation and control system 402 makes activation/deactivation decisions and transmits them to other virus shields and computing devices via application control 404. For example, signal generation and control system 402 may receive reflected sonar beams via sonar receivers and estimate a distance to a person. Signal generation and control system 402 may determine whether the distance is less than a threshold distance and activate sterilization accordingly. Based on the distance and direction from which reflected sonar beams are received, signal generation and control system 402 may activate a specific sterilizer (e.g., left sterilizer).

Likewise, depending on how many other users have virus shields in a given environment and their respective distances, signal generation and control system 402 may determine and instruct which emitters and receivers should be activated amongst multiple virus shields. The decision making between different signal generation and control systems may be based on factors such as battery (e.g., a virus shield with a lower remaining battery may deactivate a sterilizer if another virus shield can accommodate by sterilizing the area corresponding to said sterilizer), anticipated usage derived from historic usage (e.g., a virus shield that historically activates the sterilizers more frequently or for a longer period of time in a given time period and is anticipated to continue this pattern may deplete its battery faster and is thus instructed to deactivate a sterilizer if another virus shield can accommodate), shield age (e.g., as a virus shield ages, its hardware components may not be as effective and may be instructed to deactivate if another virus shield can accommodate), and model (e.g., an older version of the virus shield may have less powerful emitters and may be instructed to deactivate if another virus shield can accommodate).

In some aspects, the communication between different virus shields also enables the generation of crowd density information. For example, signal generation and control system 402 may gather distances captured between the wearer and different people. This distance information may be uploaded to a cloud server via application control 404. The cloud server may also gather distance information from other virus shields as well. This collected information may be synchronized by virus shield applications that can then determine and provide crowd/population densities in different locations.

Figure 5:
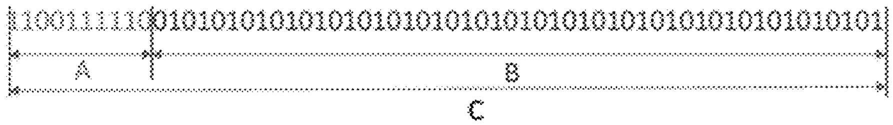
FIG. 5 is a diagram illustrating a sonar key gated packet.

FIG. 5 is diagram 500 illustrating a sonar key gated packet. The total gated ultrasound packet for sonar is C=A+B. In an exemplary aspect, every data symbol in packet C has a fixed time duration that establishes a packet frequency for ultrasound between 25 MHz and 100 MHz (i.e., the range that most affects viruses such as Covid-19). In this range, an ultrasound signal causes the lipid that holds virus RNA inside to burst. Fixed duration key packet header A has a predetermined key expressed in binary. Fixed duration packet body B (e.g., 010101 . . . ) has a pattern that creates a coherent frequency ultrasound packet.

In terms of sterilization, the sterilizing packet does not require a gated key for identification. In some aspects, the sterilizing packets and the sonar packets use different ultrasound frequencies to limit interference. In some aspects, the sterilizing packets and the sonar packets use different time slots to limit interference.

In some aspects, the key gated packet is used to differentiate between sonar signals that may be used nearby by different people wearing a similar virus shield. The key for each gate should thus be unique to every virus shield as a serial number. In some aspects, the same key gate can be used for all pulses emitted from one virus shield. This is because reflections always come back after an emission and system 402 is configured to measure the delay and calculate the distance of the reflection. Accordingly, the virus shield will send a sonar signal, and then wait for a reflection. Subsequent to receiving a reflection and determining whether the reflection can be accepted or rejected (see FIG. 6 description) to calculate distance, a subsequent sonar signal may be emitted by the virus shield.

In some aspects, the virus shield may change the key periodically. For example, the virus shield may change the key if an anticipated reflection was not received within a threshold period of time or if the amplitude of the reflected signal is below a threshold amplitude. Both cases signify that the object from which the reflection originates from is too far.

Figure 6:
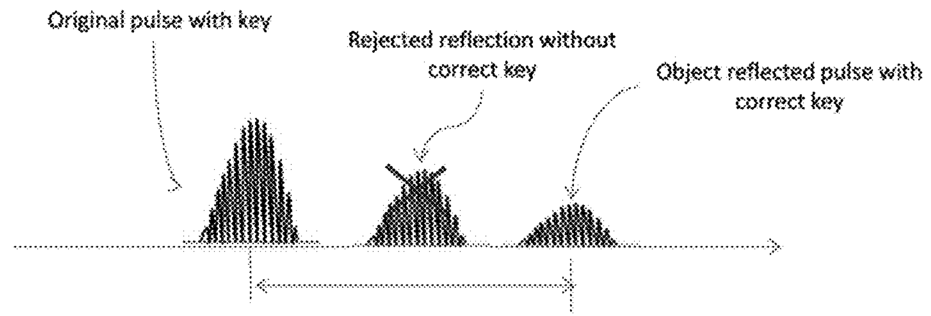
FIG. 6 is a diagram illustrating a separated ultrasound pulses.

FIG. 6 is diagram 600 illustrating separated ultrasound pulses. As shown in diagram 600, incoming reflections are separated by a correct frequency of a binary pattern. Signal generation and control system 402 may identify a correct length packet by counting the number of symbols in packet. Signal generation and control system 402 may further identify a gated key sequence and measure a time distance between correct gated sequenced packets. An incorrect gated sequence pulse is shown as the middle pulse in diagram 600. Signal generation and control system 402 is configured to reject reflections without the correct key (e.g., header A). Here, distance analysis only involves looking at time slots predetermined for sonar packets and the distance to a subject (e.g., person 102*a*) is a function of and is calculated based on time reflections of correct packets.

For example, the speed of sound is 343 m/s. For a 2-meter (2 m) distance, the sound has to travel 2 m towards the object and 2 m from the object back to the microphone. The total travel distance is 4 m. For a 4 m distance, the time for sound to reflect back is 4 m/343 m=0.01166 seconds or 11.66 milliseconds (i.e., V=D/T). Thus, if the threshold for initializing a sterilizing emission is 2 meters, the virus shield searches for reflections that are at most 11.66 ms after the initial packet emission. If a reflection is detected (recognized by the unique key), sterilization is initiated and may continue until the reflections are no longer detected.

In some aspects, each virus shield has its own individual keys embedded in the sonar beams to prevent interference (i.e., use individual key-based sonar to differentiate correct ultrasound reflections).

Figure 7:
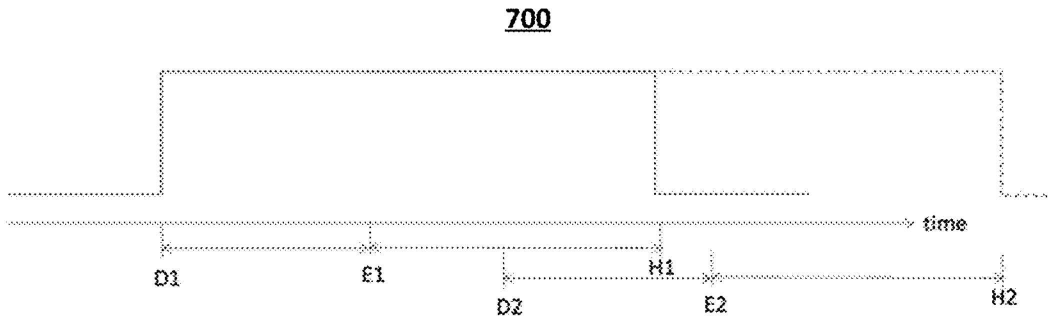
FIG. 7 is a diagram illustrating a time period for sterilization based on subject proximity.

FIG. 7 is diagram 700 illustrating a time period for sterilization based on subject proximity. In diagram 700, D1 represents the time point for sterilization activation based on subject proximity detection (e.g., sterilization beams activated in response to detecting person 102*a*). E1 represents the end point of subject proximity detection. For example, by time E1, person 102*a* may move away from wearer 101. The time between E1 and H1 is additional time added to continue the sterilization action even if a subject (e.g., person 102*a*) is no longer detected. This additional time for sterilization is optional, but may be utilized because certain viruses linger in the air even after the subject has exited the environment or has moved out of the sonar emitter range.

Suppose that a new subject (e.g., person 102*b*) is detected at time D2 (i.e., between E1 and H1), signal generation and control system 402 may extend the post detection hysteresis from point E2 to point H2. In some aspects, signal generation and control system 402 may stop sterilization when no more subject detection events are generated in the Ex-Hx time interval.

Figure 8:
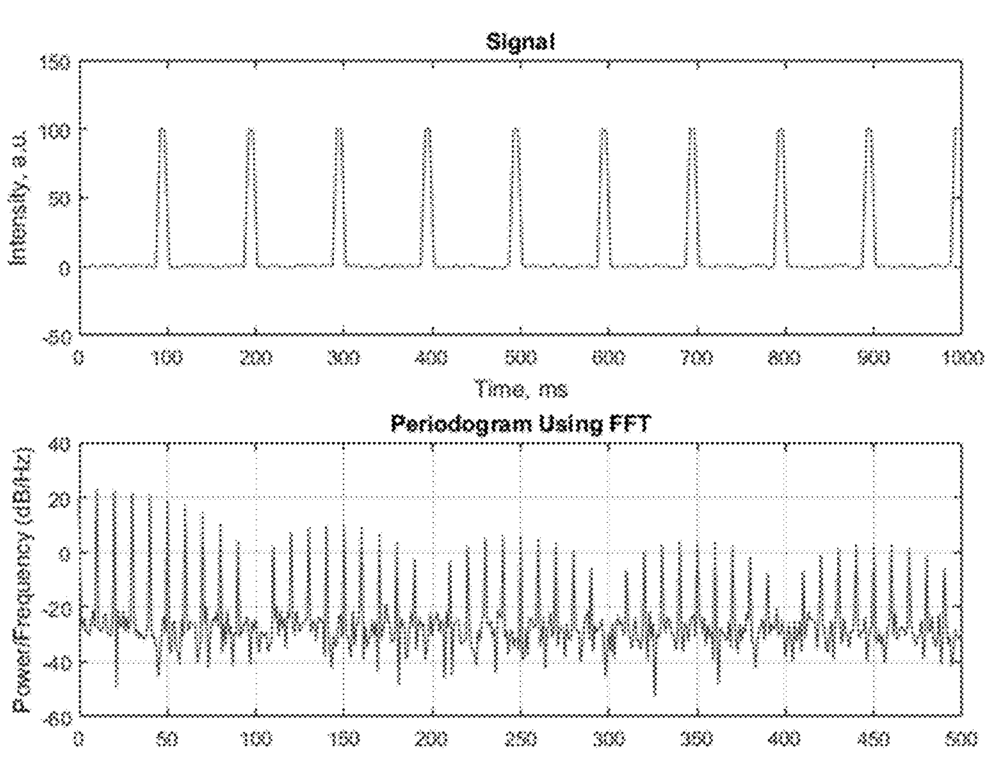
FIG. 8 is a diagram illustrating the generation of a harmonics-filled spectrum by randomizing square wave duty cycle.
Figure 8:
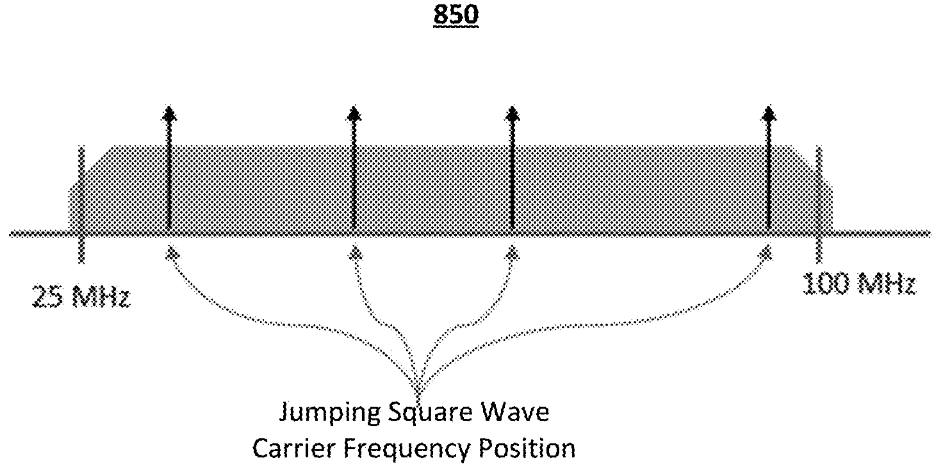

FIG. 8 depicts diagram 800 and diagram 850. Diagram 800 depicts the generation of a harmonics-filled spectrum by selecting or randomizing square wave duty cycle, frequency position, and emission time for ultrasound frequency pattern sterilizing signals. Diagram 850 depicts jumping square wave carrier frequency positions. In general, a square wave carrier with a narrow duty cycle generates several harmonics.

In terms of emitting sterilization beams, because the virus shield is driven by a microprocessor, any waveform and wave shape can be generated. In an exemplary aspect, signal generation and control system 402 broadcasts a few (e.g., 5-20) square wave carriers in the band from 25 MHz to 100 MHz to populate this bandwidth with many harmonics carriers. This proves to be deadly for any relative virus size. Depending on microprocessor capability and power availability, signal generation and control system 402 may generate multiple carriers at the same time. Diagram 850 shows "jumping" square wave carrier frequency positions that fill in the spectrum with harmonics.

In some aspects, the duty cycle, frequency position, and jumping time is random (e.g., every 10 ms to 100 ms). In some aspects, the duty cycle, frequency positions, and the amplitude of the square wave can be constantly changed and randomized to create a spectrum fill up similar to "white noise." In fact, if the microprocessor is capable, it can also generate "white noise" between 25 MHz to 100 MHz. For example, a frequency position of the at least one square wave carrier may be changed by system 402 a number of times (e.g., 10 times) within a threshold period of time (e.g., 100 ms).

In some aspects, the duty cycle, frequency positions, and the amplitude of the square wave can be adjusted by system 402 (i.e., selected and periodically changed) based on the virus the shield is configured to eliminate. For example, there may be specific configurations of the square wave that will be more effective against some viruses than against other viruses. The configurations may be preset based on virus characteristics. The mechanics here is that zipping frequency and/or its harmonics mechanically vibrate a protective lipid of the virus to cause it to burst. A particular combination of frequency and amplitude will be enough to burst a lipid bubble for given virus in a short period of time. A jumping square wave carrier may thus be able to hit a particular frequency that is enough to eliminate a virus. Although white noise should accomplish this as well, it may require much more power and drain battery life faster. Thus, quickly jumping through signal frequency emissions at selected frequency locations may be a more efficient approach compared to white noise using the same energy for emission.

Figure 9:
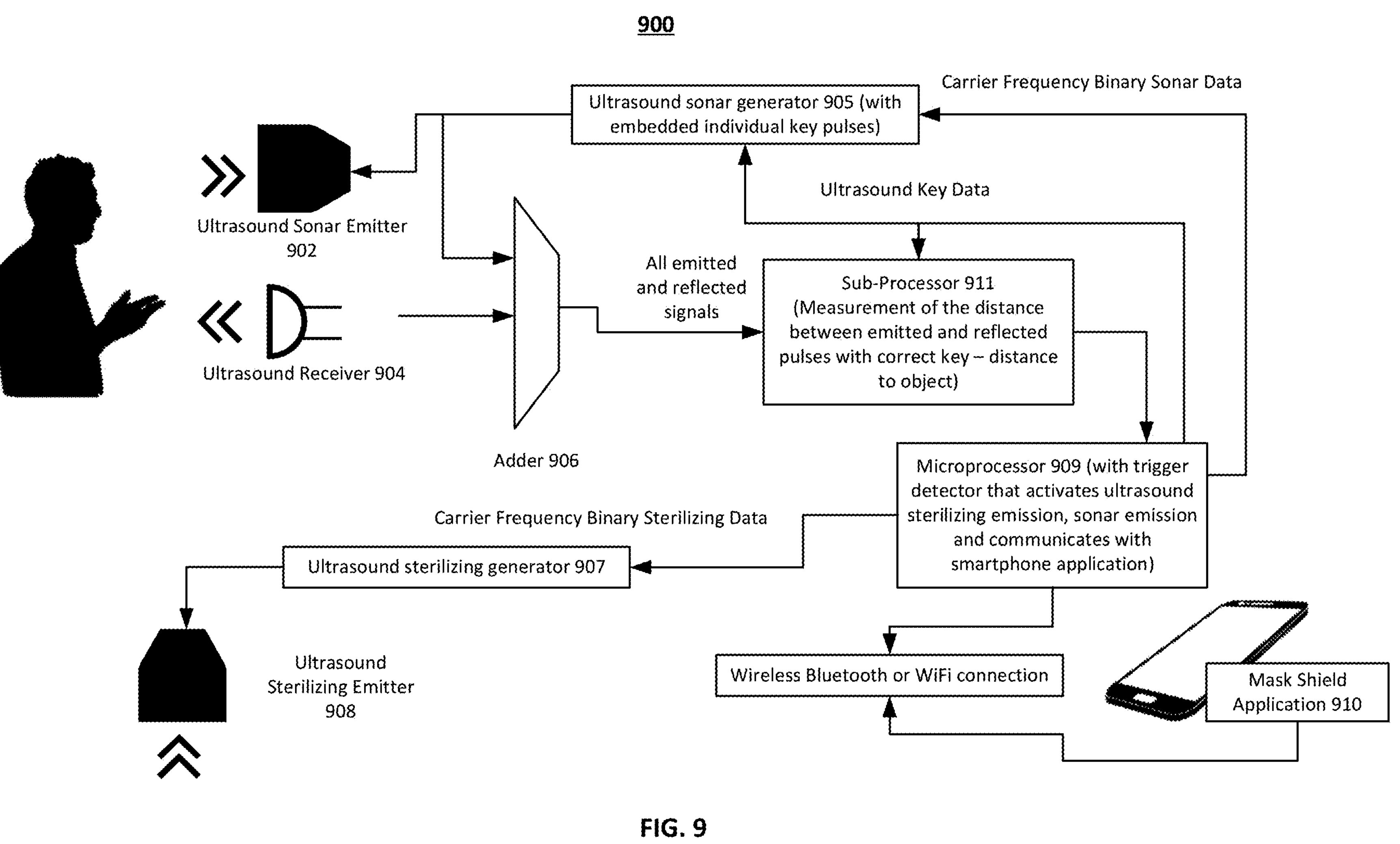
FIG. 9 is a block diagram illustrating a system for sterilizing a virus using an ultrasound-based virus shield.

FIG. 9 is a block diagram illustrating system 900 for sterilizing a virus using an ultrasound-based virus shield. In system 900, microprocessor 909 is configured to create and modify individual keys (e.g., ultrasound key data). Microprocessor 909 supplies ultrasound sonar generator 905 with carrier frequency binary sonar data, and ultrasound sonar generator 905 creates a sonar frequency and inserts the ultrasound key data into the sonar signal. The sonar signal is emitted by ultrasound sonar emitter 902. Subsequently, ultrasound receiver 904 receives reflected sonar beams.

Adder 906 receives all emitted and reflected signals and provides them to sub-processor 911, which analyzes incoming ultrasound reflections. In some aspects, sub-processor 911 may be a part of the virus shield or may be on a cloud server. Sub-processor 911 may identify reflections with a correct key and measure time between correct reflections to estimate the distance to the subject.

Microprocessor 909 receives the estimated distance and determines whether to activate ultrasound sterilizing emission (e.g., is the estimated distance less than a threshold distance). Microprocessor 909 provides carrier frequency binary sterilizing data to ultrasound sterilizing generator 907, which creates a sterilizing frequency. Ultrasound sterilizing emitter 908 emits the sterilizing signal.

Microprocessor 909 may further communicate all data to a computing device (e.g., a smartphone) through Bluetooth or Wi-Fi. As mentioned previously, the cloud-based virus shield application 910 may aggregate individual virus shield reports from a plurality of virus shields to perform a statistical analysis of population density. The virus shield application 910 may offer open API to collaborate with other shield systems and/or information/alert applications. In some aspects, application 910 connected to the system may become active on the command from other computing devices or cloud services.

Figure 10:
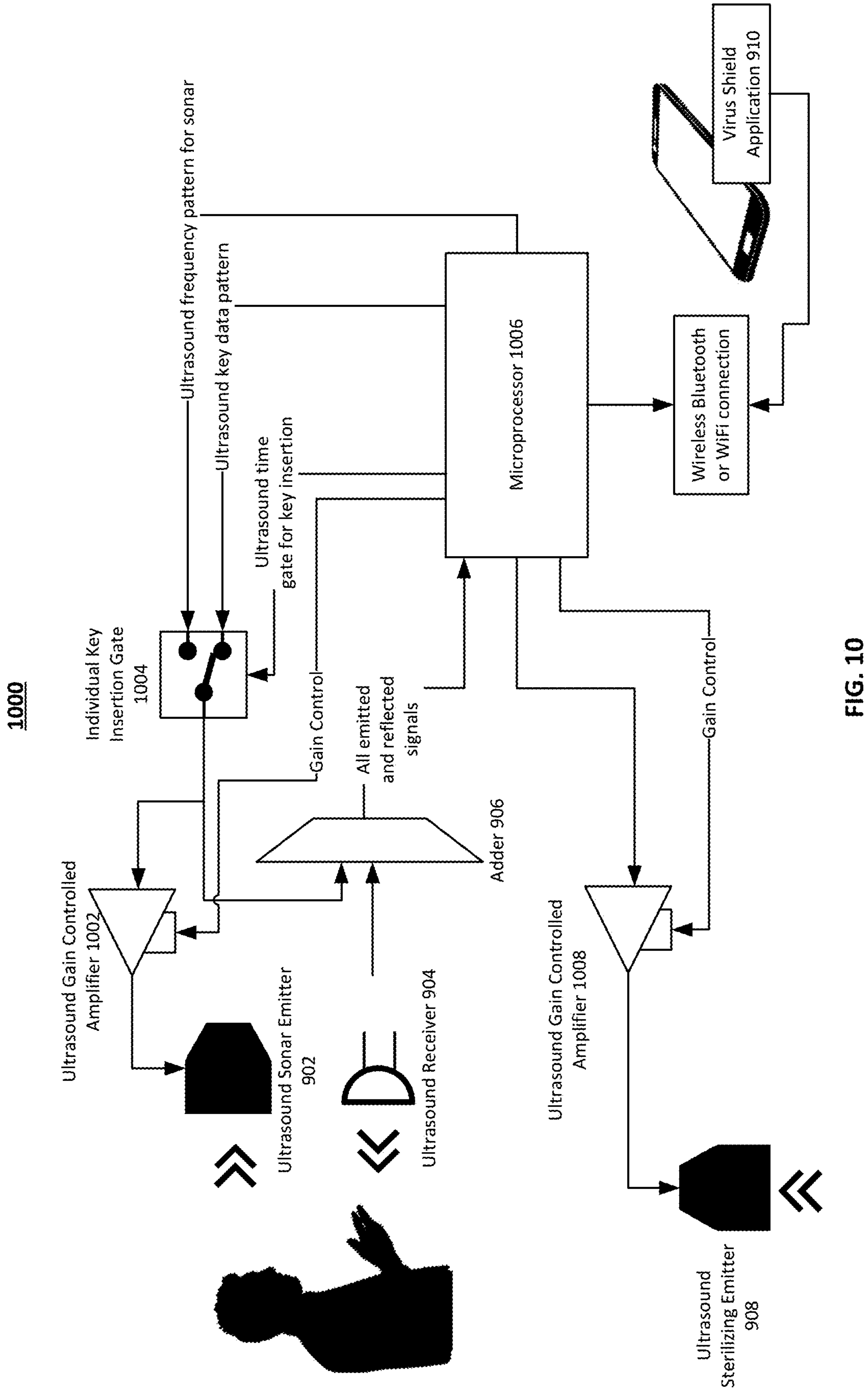
FIG. 10 is a block diagram illustrating a system for sterilizing a virus using an ultrasound-based virus shield comprising gain controlled amplifiers.

FIG. 10 is a block diagram illustrating a system 1000 for sterilizing a virus using an ultrasound-based virus shield comprising gain controlled amplifiers. In system 1000, microprocessor 1006 may create a time gating function to insert a key (i.e., ultrasound key data) into a sonar signal. This is represented by individual key insertion gate 1004, which allows either ultrasound key data pattern or ultrasound frequency pattern for sonar based on the time gating function. The functionality of ultrasound sonar emitter 902, ultrasound receiver 904, adder 906, microprocessor 1006, application 910, and ultrasound sterilizing emitter 908 is carried over from system 900 into system 1000.

In system 1000, microprocessor 1006 further modifies sonar and sterilizing frequencies and gain (using ultrasound gain controlled amplifier 1002 and ultrasound gain controlled amplifier 1008, respectfully) to minimize interference between the respective beam types. Microprocessor 909 further modifies sonar and sterilizing frequencies and gain to maximize subject detection and the sterilizing effect. For example, for objects further away, the amplitude of an output signal needs to be increased (i.e., adjust gain) such that the reflections are not too weak to detect. The amplitude of an output signal may in contrast need to be decreased to conserve the battery of virus shields as higher amplitudes require more power. In some aspects, the amplitude may be adjusted based on remaining battery life of a virus shield (i.e., may proportionally decrease alongside battery percentage).

Accordingly, the amplitude can be variable. That may be needed for power considerations, as described above, or to adopt to zipping speaker bandwidth linearity. For example, if a speaker is less efficient at a certain frequency (e.g., 45 MHz), the virus shield may increase the amplitude for a signal emitted at 45 MHz.

Figures 11A, 11B, 11C:
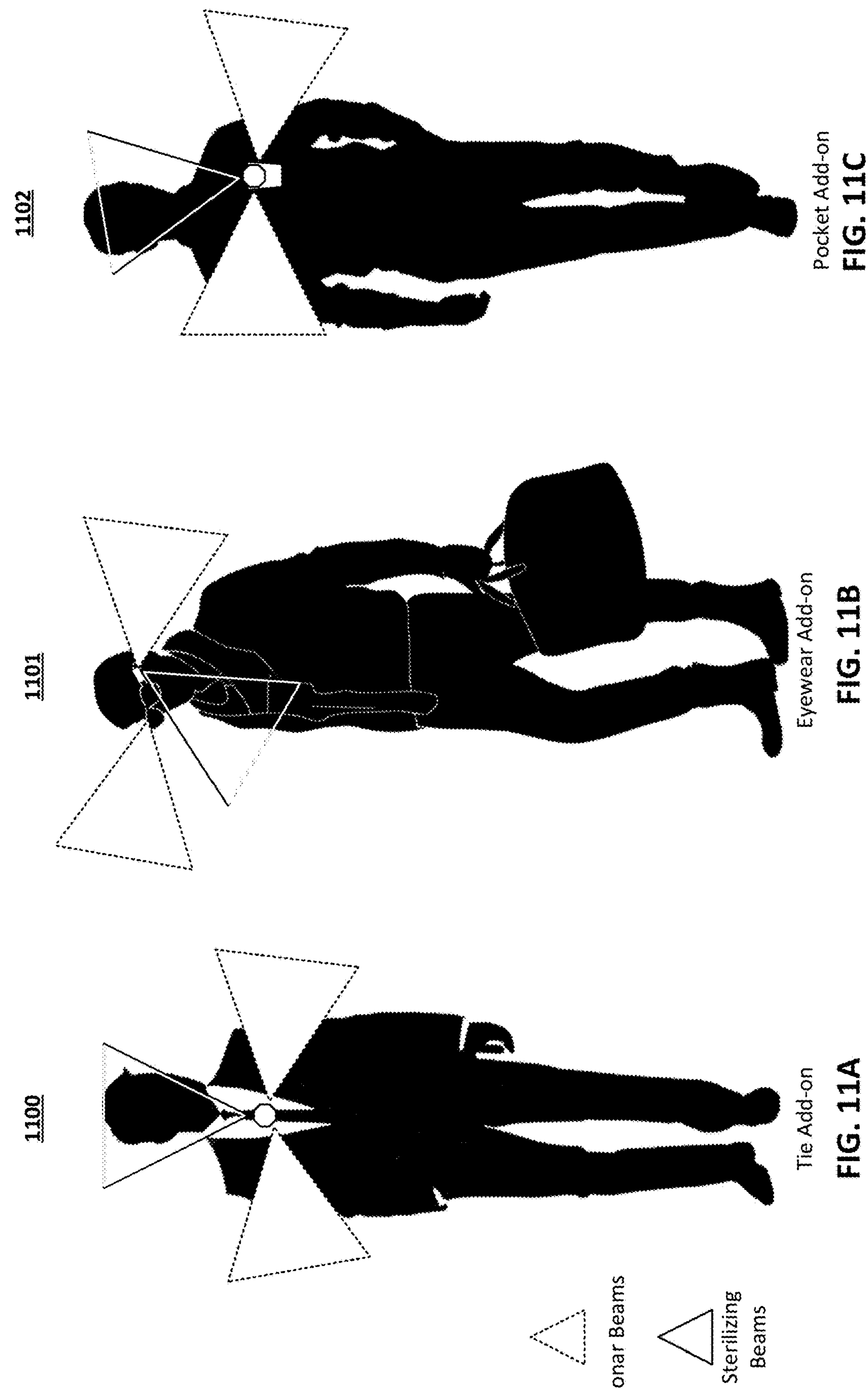
FIG. 11A is a diagram illustrating usage of a variation of the ultrasound-based virus shield attached to a tie.
FIG. 11B is a diagram illustrating usage of a variation of the ultrasound-based virus shield attached to eyewear.
FIG. 11C is a diagram illustrating usage of a variation of the ultrasound-based virus shield attached to a shirt pocket.

FIG. 11A is diagram 1100 illustrating usage of a variation of the ultrasound-based virus shield attached to a tie. FIG. 11B is diagram 1101 illustrating usage of a variation of the ultrasound-based virus shield attached to eyewear. FIG. 11C is diagram 1102 illustrating usage of a variation of the ultrasound-based virus shield attached to a shirt pocket. In each of FIGS. 11A, 11B, and 11C, the sterilizing beams are directed towards the face of the wearer and the sonar beams have at least 180 degrees of coverage (from the left side of the wearer to the right side of the wearer). The virus shield may be attached to the glasses, tie, pocket, etc., using an attaching component such as a clip, a pin, or an adhesive.

Figure 12:
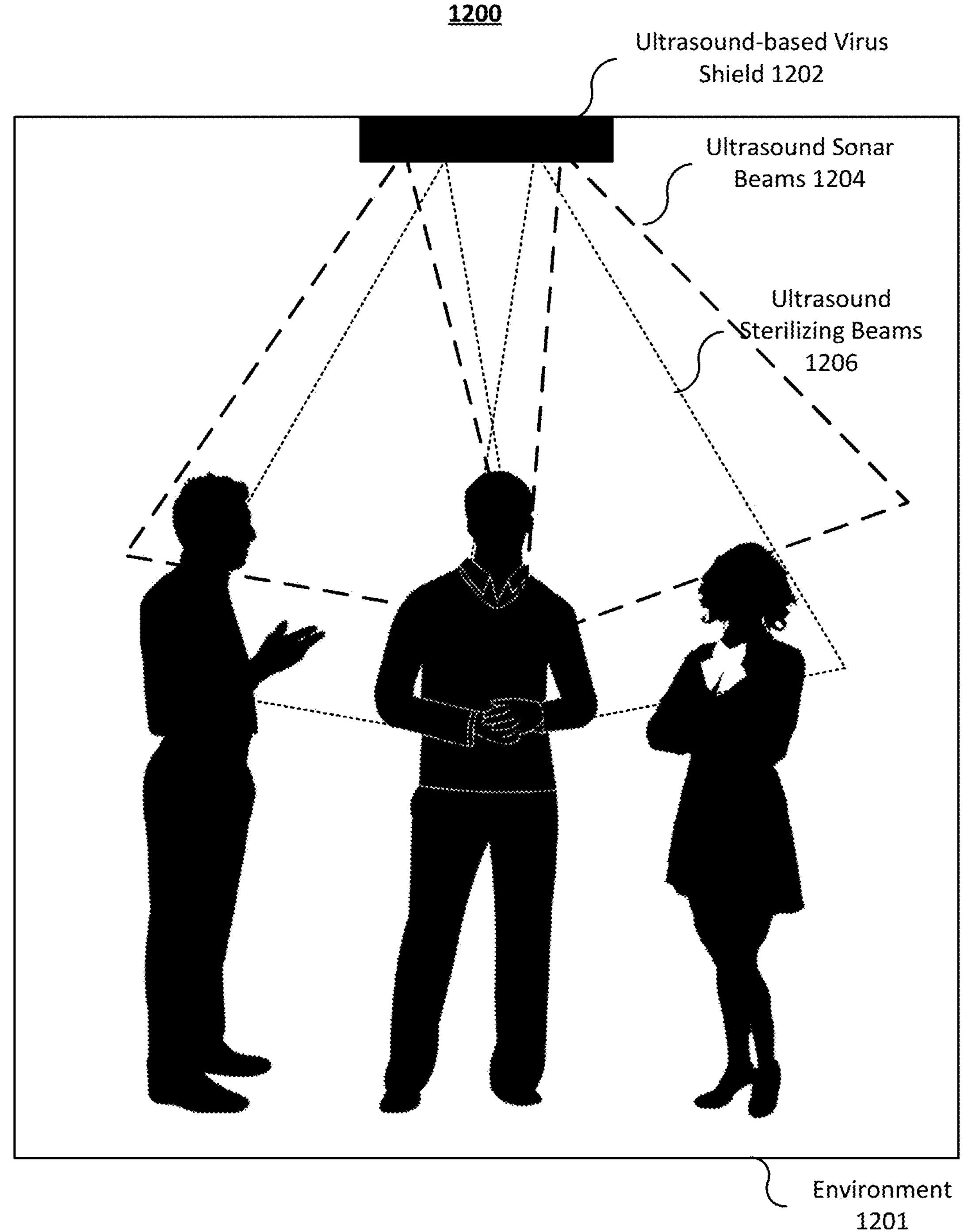
FIG. 12 is a diagram illustrating usage of a variation of the ultrasound-based virus shield attached to the ceiling of an environment.

FIG. 12 is diagram 1200 illustrating usage of a variation of the ultrasound-based virus shield attached to the ceiling of an environment. In previously-described variations of the virus shield, the virus shield is seen attached to the wearer by a strap or is attached to the attire of the wearer. The virus shield may also be provided as a handheld unit or a standalone desktop.

In addition to these variations, the virus shield may be installed in an environment (e.g., a conference room, an elevator, a lobby, transportation vehicles, concert halls, apartments, etc.). In this variation, the virus shield may be attached using an attaching component such as a mounting bracket (e.g., screws, bolts, etc.).

In diagram 1200, ultrasound-based virus shield 1202 is installed on the ceiling of environment 1201. Shield 1202 emits ultrasound sonar beams 1204 (in some aspects, periodically) to detect subjects in environment 1201, and in response to detecting at least one subject, emits ultrasound sterilizing beams 1206. In diagram 1200, all circuitry of shield 1202 may be mounted to the ceiling.

Figure 13:
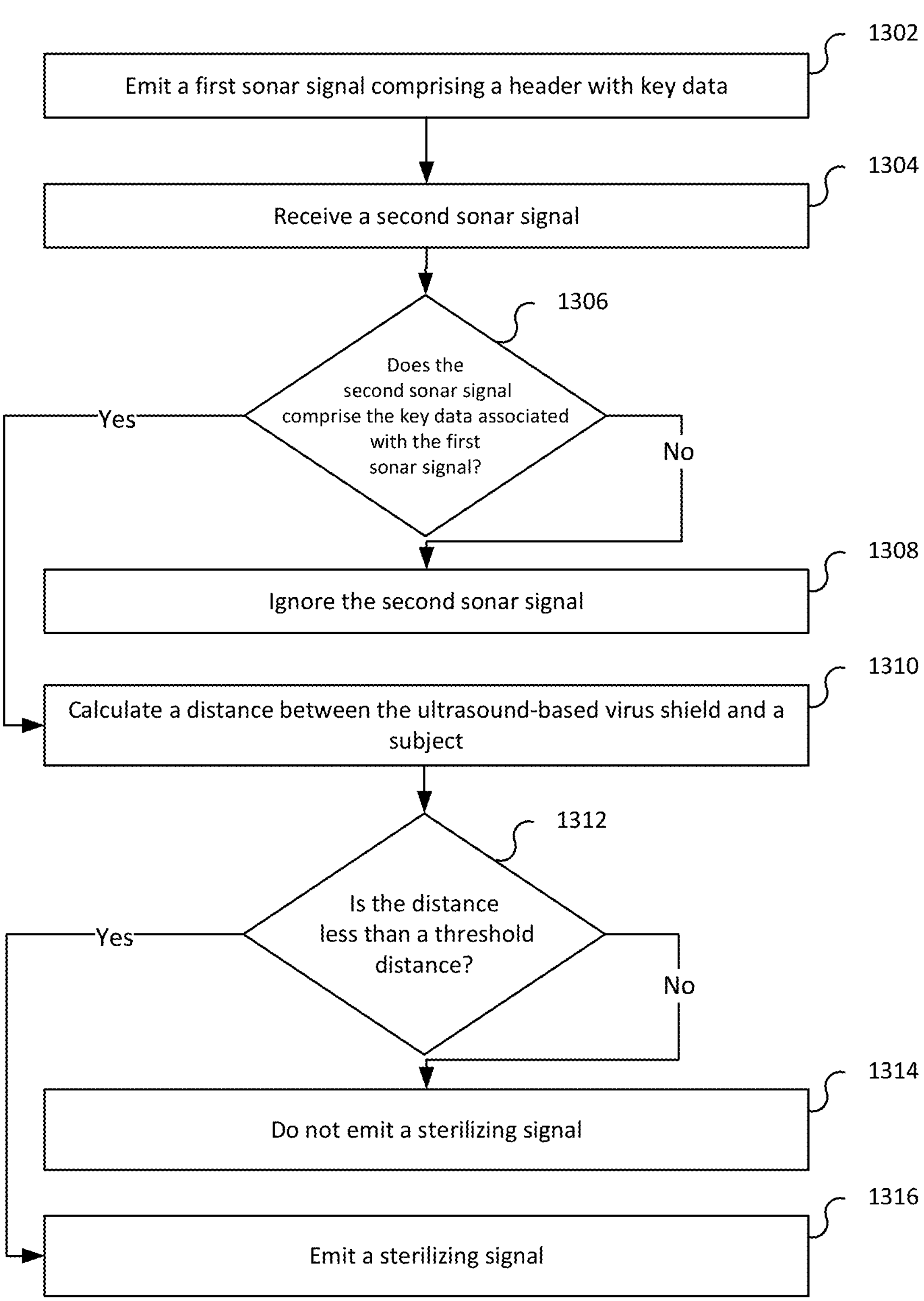
FIG. 13 is a block diagram illustrating a method for sterilizing a virus using an ultrasound-based virus shield.

FIG. 13 is a block diagram illustrating a method 1300 for sterilizing a virus using an ultrasound-based virus shield.

At 1302, ultrasound-based virus shield 104 emits a first sonar signal comprising a header with key data.

At 1304, ultrasound-based virus shield 104 receives a second sonar signal.

At 1306, ultrasound-based virus shield 104 determines whether the second sonar signal comprises the key data associated with the first sonar signal. In response to determining that the second sonar signal does not comprise the key data, method 1300 advances to 1308, where ultrasound-based virus shield 104 ignores the second sonar signal and may subsequent receive a different sonar signal. In response to determining that the second sonar signal does comprise the key data (indicative of a correct reflection signal), method 1300 advances to 1310, where ultrasound-based virus shield 104 calculates a distance between the ultrasound-based virus shield and a subject.

At 1312, ultrasound-based virus shield 104 determines whether the distance (e.g., 1 meter) calculated is less than a threshold distance (e.g., 2 meters). In response to determining that the distance calculated is not less than the threshold distance, method 1300 advances to 1314, where ultrasound-based virus shield 104 determines not to emit a sterilizing signal. However, in response to determining that the distance calculated is less than the threshold distance (e.g., person 102*a* is in close proximity), method 1300 advances to 1316, where ultrasound-based virus shield 104 emits a sterilizing signal.

Figure 14:
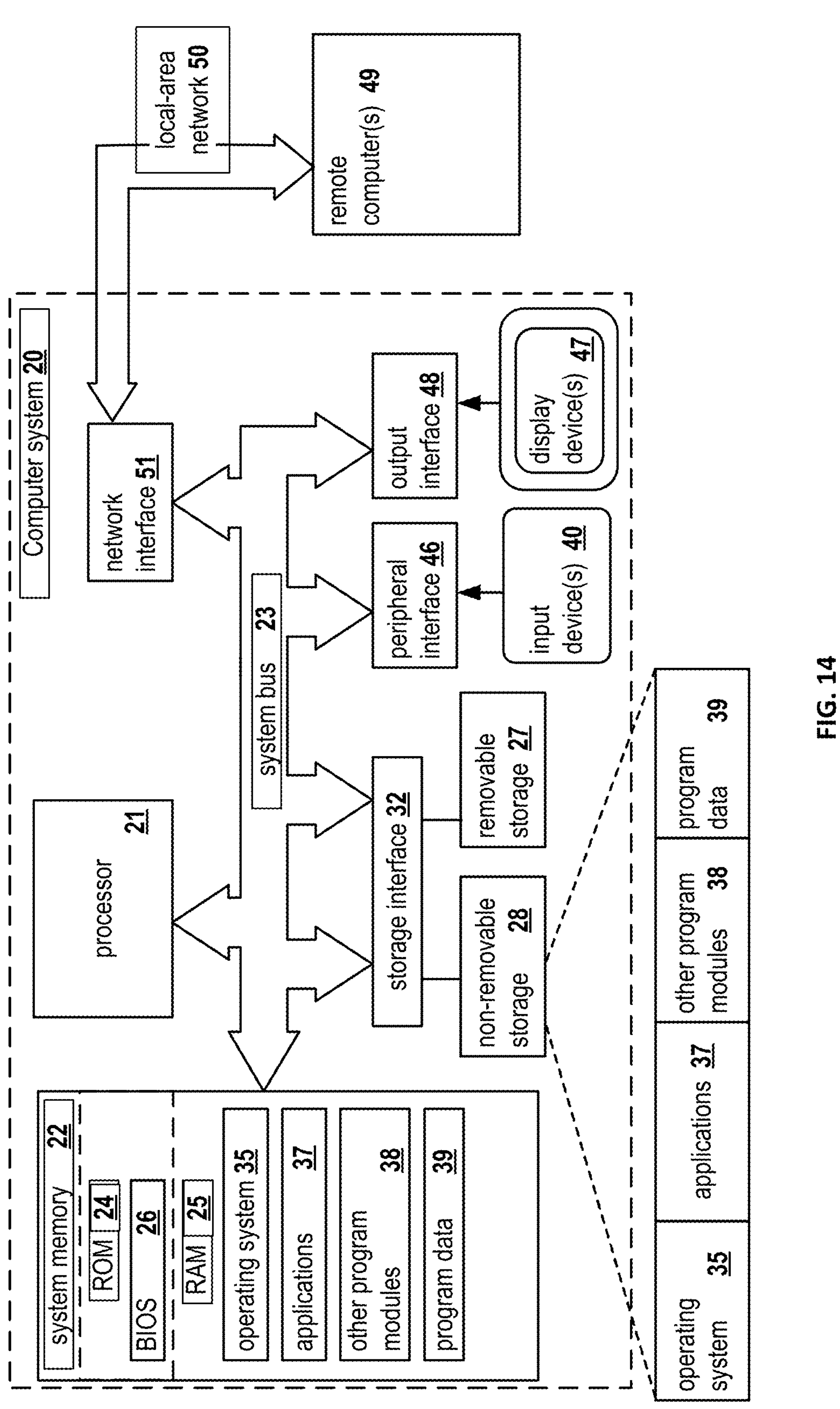
FIG. 14 presents an example of a general-purpose computer system on which aspects of the present disclosure can be implemented.

FIG. 14 is a block diagram illustrating a computer system 20 on which aspects of systems and methods for sterilizing a virus using an ultrasound-based virus shield may be implemented in accordance with an exemplary aspect. Computer system 20 may be an ultrasound-based virus shield. Accordingly, computer system 20 may run virus shield application 910 and/or may execute signal generation and control system 402.

As shown, the computer system 20 includes a central processing unit (CPU) 21, a system memory 22, and a system bus 23 connecting the various system components, including the memory associated with the central processing unit 21. The processor 21 (e.g., a microprocessor) may execute one or more computer-executable code implementing the techniques of the present disclosure. For example, any of commands/steps discussed in FIGS. 1-13 may be performed by processor 21. The system memory 22 may be any memory for storing data used herein and/or computer programs that are executable by the processor 21. The system memory 22 may include volatile memory such as a random access memory (RAM) 25 and non-volatile memory such as a read-only memory (ROM) 24, etc., or any combination thereof. The basic input/output system (BIOS) 26 may store the basic procedures for transfer of information between elements of the computer system 20, such as those at the time of loading the operating system with the use of the ROM 24.

The computer system 20 may include one or more storage devices such as one or more removable storage devices 27, one or more non-removable storage devices 28, or a combination thereof. The one or more removable storage devices 27 and non-removable storage devices 28 are connected to the system bus 23 via a storage interface 32.

The system memory 22, removable storage devices 27, and non-removable storage devices 28 of the computer system 20 may be used to store an operating system 35, additional program applications 37, other program modules 38, and program data 39. The computer system 20 may include a peripheral interface 46 for communicating data from input devices 40, such as a voice input device or a touch input device. A display device 47 such as an integrated display may also be connected to the system bus 23 across an output interface 48, such as a video adapter.

The computer system 20 may operate in a network environment, using a network connection to one or more remote computers 49. The remote computer (or computers) 49 may be other virus shields or servers comprising most or all of the aforementioned elements in describing the nature of a computer system 20. Other devices may also be present in the computer network, such as, but not limited to, routers, network stations, peer devices or other network nodes. The computer system 20 may include one or more network interfaces 51 or network adapters for communicating with the remote computers 49 via one or more networks such as a local-area computer network (LAN) 50, a wide-area computer network (WAN), an intranet, and the Internet.

Aspects of the present disclosure may be a system, a method, and/or a computer program product. The computer program product may include a computer readable storage medium (or media) having computer readable program instructions thereon for causing a processor to carry out aspects of the present disclosure. The computer readable storage medium can be a tangible device that can retain and store program code in the form of instructions or data structures that can be accessed by a processor of a computing device, such as the computing system 20.

In the interest of clarity, not all of the routine features of the aspects are disclosed herein. It would be appreciated that in the development of any actual implementation of the present disclosure, numerous implementation-specific decisions must be made in order to achieve the developer's specific goals, and these specific goals will vary for different implementations and different developers. It is understood that such a development effort might be complex and time-consuming, but would nevertheless be a routine undertaking of engineering for those of ordinary skill in the art, having the benefit of this disclosure.

Furthermore, it is to be understood that the phraseology or terminology used herein is for the purpose of description and not of restriction, such that the terminology or phraseology of the present specification is to be interpreted by the skilled in the art in light of the teachings and guidance presented herein, in combination with the knowledge of those skilled in the relevant art(s). Moreover, it is not intended for any term in the specification or claims to be ascribed an uncommon or special meaning unless explicitly set forth as such.

The various aspects disclosed herein encompass present and future known equivalents to the known modules referred to herein by way of illustration. Moreover, while aspects and applications have been shown and described, it would be apparent to those skilled in the art having the benefit of this disclosure that many more modifications than mentioned above are possible without departing from the inventive concepts disclosed herein.

The invention claimed is:

1. An ultrasound-based virus shield, comprising:

an ultrasound sonar emitter configured to emit a first sonar signal comprising a header with key data, wherein the key data is unique to the ultrasound-based virus shield;

an ultrasound sonar receiver configured to receive a plurality of second sonar signals;

a processor configured to:

determine, for each respective second sonar signal of the plurality of second sonar signals, whether the respective second sonar signal comprises the key data by identifying a gated key sequence in a header of the respective second sonar signal;

reject second sonar signals that do not comprise the key data to prevent interference from sonar signals emitted by other ultrasound-based virus shields;

calculate a distance between the ultrasound-based virus shield and a subject based on a time difference between emission of the first sonar signal and receipt of second sonar signals determined to comprise the key data; and activate an ultrasound sterilizing emitter in response to determining that the distance calculated is less than a threshold distance; and the ultrasound sterilizing emitter configured to emit a sterilizing signal.

2. The ultrasound-based virus shield of claim 1, the processor is further configured to calculate the distance by executing a function that converts the time difference to the distance.

3. The ultrasound-based virus shield of claim 1, wherein the ultrasound sonar emitter is configured to emit the sterilizing signal until the distance between the ultrasound-based virus shield and the subject is not greater than the threshold distance.

4. The ultrasound-based virus shield of claim 3, wherein the ultrasound sonar emitter is configured to continue emitting the sterilizing signal after the distance between the ultrasound-based virus shield and the subject becomes greater than the threshold distance.

5. The ultrasound-based virus shield of claim 1, wherein the ultrasound sonar emitter and the ultrasound sterilizing emitter emit the first sonar signal and the sterilizing signal, respectively, at different ultrasound frequencies to limit interference.

6. The ultrasound-based virus shield of claim 1, wherein the ultrasound sonar emitter and the ultrasound sterilizing emitter emit the first sonar signal and the sterilizing signal, respectively, at different time slots to limit interference.

7. The ultrasound-based virus shield of claim 1, wherein the sterilizing signal comprises a broadcast of at least one square wave carrier in a frequency band.

8. The ultrasound-based virus shield of claim 7, wherein a duty cycle, a frequency position, and an amplitude of the at least one square wave carrier is adjustable based on virus characteristics that the ultrasound-based virus shield is configured to eliminate.

9. The ultrasound-based virus shield of claim 7, wherein a frequency position of the at least one square wave carrier is changed a number of times within a threshold period of time.

10. The ultrasound-based virus shield of claim 1, further comprising:

a communication component configured to transmit signal and distance information to a virus shield application installed on a computing device.

11. The ultrasound-based virus shield of claim 1, further comprising:

a communication component configured to connect with a second ultrasound-based virus shield within a connective range; and wherein the processor is further configured to instruct the second ultrasound-based virus shield to not activate a second ultrasound sterilizing emitter of the second ultrasound-based virus shield in response to determining that the ultrasound sterilizing emitter of the ultrasound-based virus shield is emitting the sterilizing signal.

12. The ultrasound-based virus shield of claim 11, wherein the processor is further configured to instruct the second ultrasound-based virus shield to not activate the second ultrasound sterilizing emitter in further response to determining that a remaining battery life of the second ultrasound-based virus shield is less than a remaining battery life of the ultrasound-based virus shield.

13. The ultrasound-based virus shield of claim 11, wherein the processor is further configured to instruct the second ultrasound-based virus shield to not activate the second ultrasound sterilizing emitter in further response to determining that an anticipated usage of the second ultrasound sterilizing emitter is greater than an anticipated usage of the ultrasound sterilizing emitter.

14. The ultrasound-based virus shield of claim 1, further comprising a strap that is configured to be worn around a head or neck of a wearer.

15. The ultrasound-based virus shield of claim 14, wherein the ultrasound sonar emitter comprises multiple emitters that each emit a portion of the first sonar signal, and wherein the first sonar signal achieves 360 degree coverage around the wearer.

16. The ultrasound-based virus shield of claim 14, wherein the ultrasound sterilizing emitter directs the sterilizing signal towards a face of the wearer.

17. The ultrasound-based virus shield of claim 1, wherein the ultrasound sterilizing emitter comprises multiple emitters that each emit a portion of the sterilizing signal.

18. The ultrasound-based virus shield of claim 1, further comprising an attaching component that fixes the ultrasound-based virus shield to a surface.

19. The ultrasound-based virus shield of claim 18, wherein the attaching component is one of a clip, an adhesive, a pin, and a mounting bracket.

* * * * *